United States Patent
Hayden et al.

[11] Patent Number: 5,962,729
[45] Date of Patent: Oct. 5, 1999

[54] METHOD FOR THE MANUFACTURE OF N-PHOSPHONOMETHYLGLYCINE FROM N-PHOSPHONOMETHYLIMINODIACETIC ACID USING A CATALYTIC CARBON

[75] Inventors: Richard A. Hayden; Thomas M. Matviya, both of Pittsburgh, Pa.

[73] Assignee: Calgon Carbon Corporation, Pittsburgh, Pa.

[21] Appl. No.: 09/078,775

[22] Filed: May 14, 1998

[51] Int. Cl.$^6$ ..................................................... C07F 9/22
[52] U.S. Cl. .................. 562/17; 562/11; 562/16
[58] Field of Search .................. 562/11, 16, 17; 502/418

[56] References Cited

U.S. PATENT DOCUMENTS 3,950,402  4/1976  Franz .
3,969,398  7/1976  Hershman .
5,356,849  10/1994  Matviya ..................................... 502/180

*Primary Examiner*—Gary Geist
*Assistant Examiner*—Jean F Vollano
*Attorney, Agent, or Firm*—Titus & McConomy LLP

[57] ABSTRACT

An improved process is provided for the manufacture of N-phosphonomethylglycine from N-phophonomethyliminodiacetic acid in the presence of a molecular-oxygen containing gas utilizing a catalytically active carbonaceous char. The improvement is provided by the use of a carbonaceous char capable of rapidly decomposing hydrogen peroxide in an aqueous solution.

6 Claims, 2 Drawing Sheets

Comparison Between Peak Carbon Dioxide Concentration in Off-Gas with Peak Glyphosate Concentration in Reactor Liquid

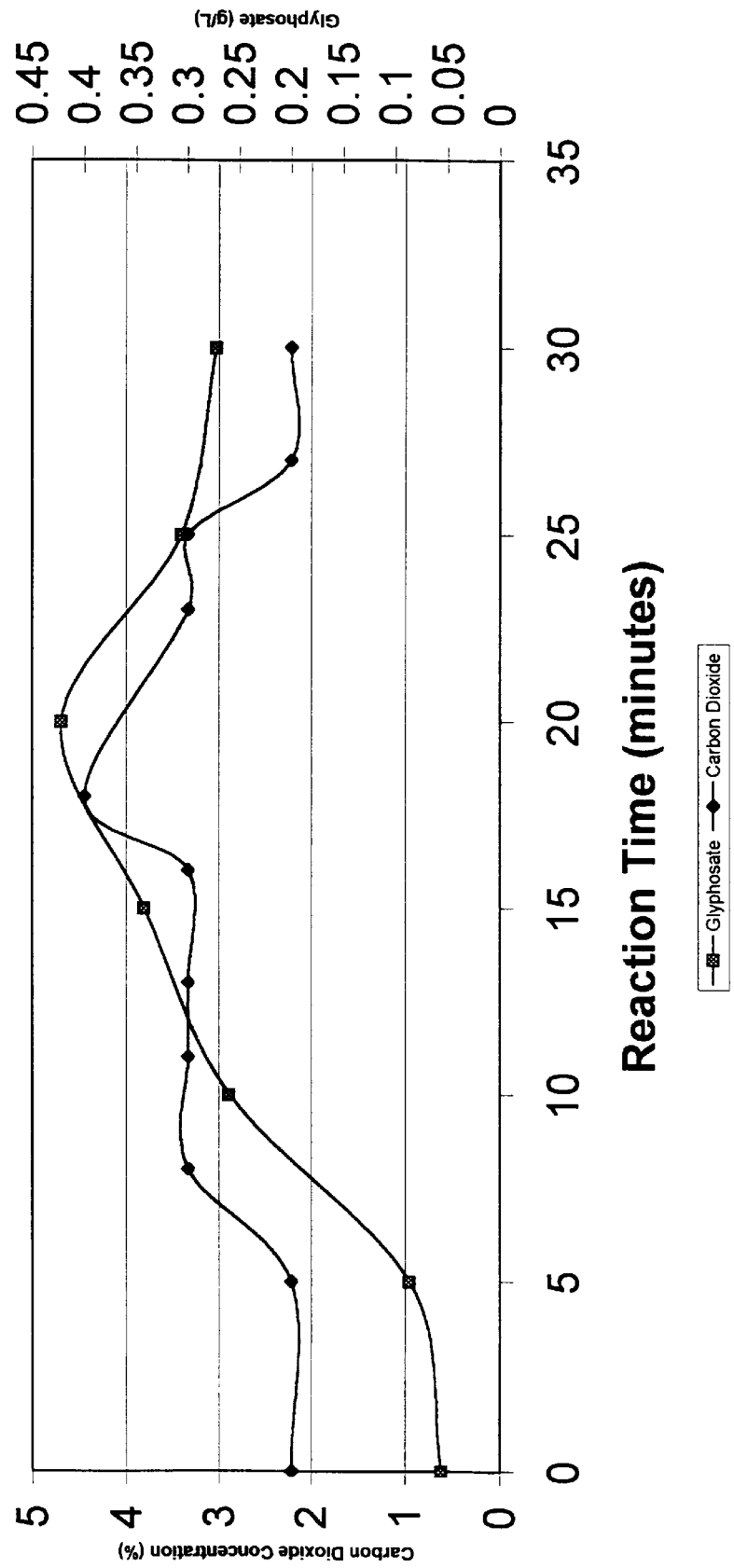

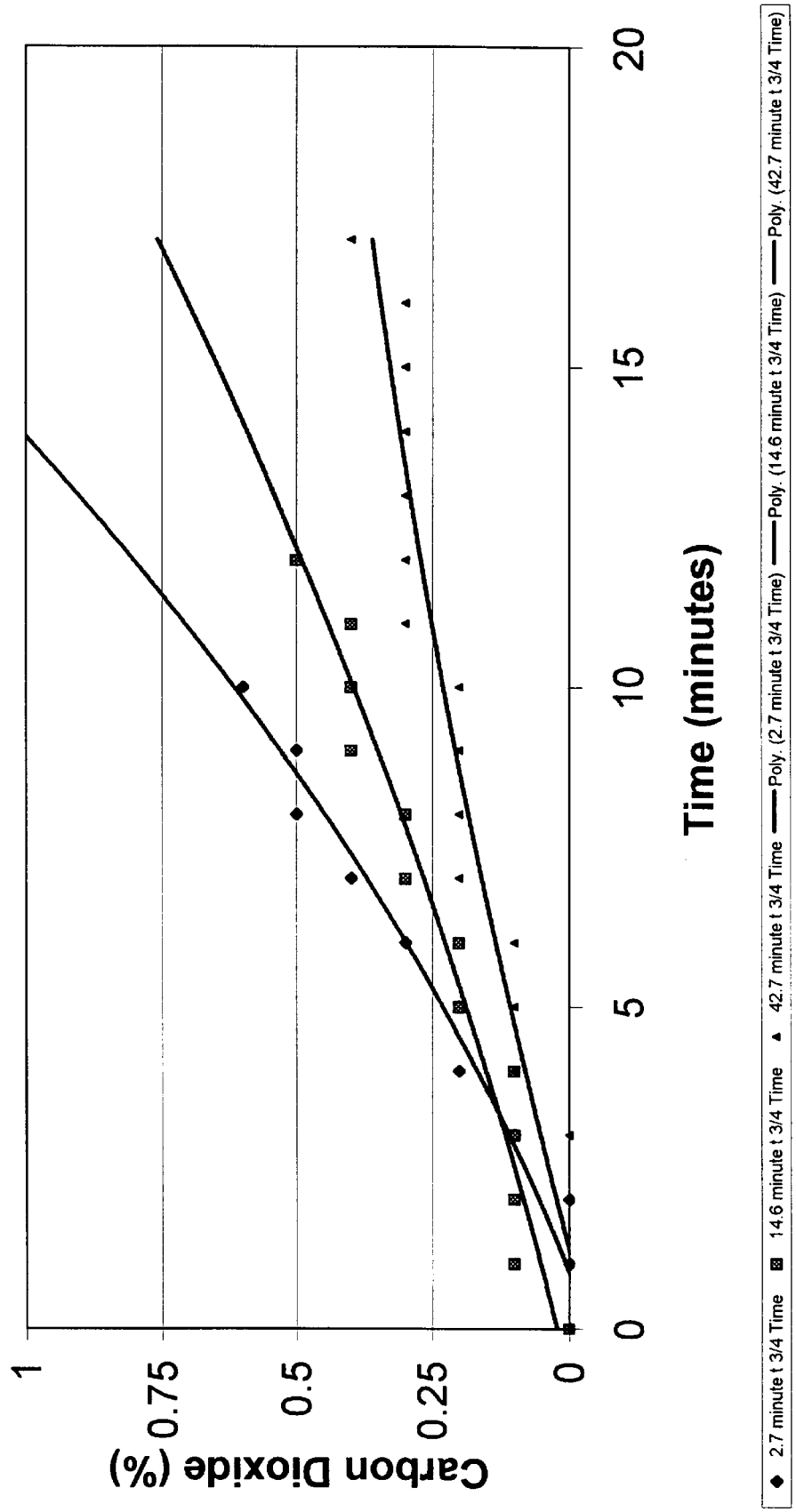

METHOD FOR THE MANUFACTURE OF N-PHOSPHONOMETHYLGLYCINE FROM N-PHOSPHONOMETHYLIMINODIACETIC ACID USING A CATALYTIC CARBON

FIELD OF INVENTION

The present invention relates the use of a catalytically active carbonaceous char for the manufacture of N-phosphonomethylglycine from N-phosphonomethyliminodiacetic acid in the presence of a molecular oxygen containing gas.

BACKGROUND OF THE INVENTION

The use of activated carbon as a catalyst to promote the formation of glyphosate by oxidation of N-phosphonomethyliminodiacetic acid is described by Hershman, U.S. Pat. No. 3,969,398, where N-phosphonomethyliminodiacetic acid is prepared by reacting iminodiacetic acid with formaldehyde and phosphoric acid. Hershman reports teaching that glyphosate is produced by the oxidation of N-phosphonomethyliminodiacetic acid in the presence of activated carbon as a catalyst according to the following proposed reaction:

$C_5H_{10}O_7NP + \frac{1}{2}O_2 \rightarrow C_3H_8O_5NP + CO_2 + CH_2O$

Rogers et al., U.S. Pat. No. 5,578,190 describes the use of carbon impregnated with various metals. The impregnated carbon is utilized to facilitate a hydrogenation reaction to produce glyphosate.

Cullen et al., International Publication Number WO 96/38455, describes the oxidation of N-phosphonomethyliminodiacetic acid with an oxidizing agent such as hydrogen peroxide in the presence of activated carbon as a catalyst. The oxidation reaction results in the production of glyphosate.

Chou, U.S. Pat. No. 4,624,937, describes the process for modifying an activated carbon capable of oxidizing tertiary amines and secondary amines in the presence of activated carbon. The process describes the modification of the activated carbon by an oxygen-containing gas and ammonia at temperatures from 800° to 1200° C. The modification process enhances the ability of the activated carbon to facilitate the oxidation of the tertiary or secondary amines.

All of the prior art for improving the production of glyphosate from N-phosphonomethyliminodiacetic acid has certain disadvantages, which make the process unattractive from a commercial standpoint. Chief among these is an inability to determine in a rapid and convenient manner the suitability of a char for such applications prior to its use, in particular the intrinsic catalytic activity of the char for glyphosate manufacture. As a result of this shortcoming, it is not possible to know or even to estimate during the preparation of a char the utility of the final product short of actual testing in the application itself.

Accordingly, it is the object of the present invention to provide an improved process for the manufacture of N-phosphonomethylglycine from N-phosphonomethyliminodiacetic acid in the presence of a gas containing molecular oxygen, such as pure oxygen, by contacting said acid with a low temperature catalytically active carbonaceous char in which the intrinsic catalytic activity of the char is measured and known prior to use. It is further the object of the present invention to estimate the intrinsic catalytic activity of the char using a test which is relatively cheap, quick, and simple in its execution and fairly indicative of the suitability of the char for the intended application.

SUMMARY OF THE INVENTION

In general, the present invention comprises an improved process for the manufacture of N-phosphonomethylglycine from N-phosphonomethyliminodiacetic acid in the presence of a molecular oxygen containing gas such as pure oxygen by contacting said media with a carbonaceous char in which the intrinsic catalytic activity of the char is measured and known prior to use. The improvement is in the use of a low temperature catalytically active carbonaceous char, which can rapidly decompose hydrogen peroxide in aqueous solution. More specifically, the carbonaceous char is preferably the low temperature char described in U.S. patent application Ser. No. 09/079,424 [attorney docket 98032] filed May 14, 1998, incorporated herein by reference. Surprisingly, when tested under conditions wherein those char properties known to affect mass transport and adsorption capacity, e.g. under conditions of nearly equivalent apparent density and iodine number, the rate at which the char can decompose hydrogen peroxide has been found to provide an indication of the utility of the char for the manufacture of glyphosate from N-phosphonomethyliminodiacetic acid. The rate of hydrogen peroxide decomposition is measured by the test described in Example 1 U.S. Pat. No. 5,470,748 Incorporated herein by reference and is reported, except where noted, as the t-¾ time, measured in minutes.

In the present invention it is found that chars having the highest utility for glyphosate manufacture are those having t-¾ times of 15 minutes or less, preferably 10 minutes or less.

BRIEF DESCRIPTION OF THE DRAWINGS

FIG. 1 is a graphical representation of the carbon dioxide concentration in the off-gas and the glyphosate in the reactor liquid.

FIG. 2 is a graphical representation of the rate of phosphonomethyliminodiacetic acid oxidation as measured by carbon dioxide evolution as a function of time for three carbons having t-¾ time values of 2.7, 14.6, and 42.7 minutes respectively.

PRESENTLY PREFERRED EMBODIMENTS

The utility of the invention is demonstrated in the following two examples. Example 1 demonstrates the correlation between the carbon dioxide concentration in the reactor off-gas and the glyphosate concentration in the reactor liquid. Example 2 demonstrates the effect of catalytic activity as measured by t ¾ time at pH 7 on the rate of carbon dioxide production in the reactor off-gas which correlates to the glyphosate concentration of the reactor liquid.

EXAMPLE 1

A sample of catalytically active material was sized so that 95% of the particles passed through a 325 mesh Tyler screen. A 0.2 gram sample of the pulverized carbon was added to the stainless steel reactor vessel of the Autoclave Engineers Eze-Seal™ Autoclave. A 0.5 gram aliquot of N-phosphonomethyliminodiacetic acid was added to the reaction flask along with 95 milliliters of deionized water. The stainless steel reactor was connected to the autoclave, and the slurry stirred at 200 rpm under a nitrogen blanket. The slurry was heated externally to 70° C. The slurry was allowed to equilibrate for approximately two hours prior to initiation of the oxidation reaction. After reaching equilibrium, pure oxygen was introduced to the reactor flask at a pressure of 60 psi. The off-gas from the reactor flask was monitored using a Nova Model 7550P7 Multi-Gas Analyzer. Liquid samples were periodically withdrawn from the reactor vessel through a sample port and analyzed for glyphosate concentration though the use of a Waters HPLC. The peak carbon dioxide concentration occurred after 18 minutes while the peak glyphosate concentration occurred at 20 minutes. A plot depicting the carbon dioxide concentration in the off-gas and the glyphosate in the reactor liquid is shown in FIG. 1.

EXAMPLE 2

Three catalytically active materials with similar properties other than catalytic activity as measured by the t-¾ time at pH 12 were tested using identical conditions to the material in Example 1. Carbon dioxide concentration in the off-gas was analyzed. Data show the rate of carbon dioxide generation was greatest for the catalytically active material with the highest catalytic activity as measured by the t-¾ time, while the least catalytically active material had the slowest carbon dioxide generation rate. Data is shown in TABLE 1 below.

TABLE 1

| Sample | Iodine Number (mg/g) | Apparent Density (g/cc) | t-¾Time (minutes) |
|---|---|---|---|
| Catalytically Active | 1075 | 0.53 | 2.7 |
| Catalytically Active | 1066 | 0.53 | 14.6 |
| Activated Carbon | 1066 | 0.53 | 42.7 |

While a presently preferred embodiment of the invention has been described in particularity, it may be otherwise embodied within the scope of the appended claims.

What is claimed is:

1. The process for the production of N-phosphonomethyl glycine (glyphosphate) which comprises contacting an aqueous solution of N-phosphonomethyliminodiacetic acid with a gas containing molecular oxygen at an elevated temperature to initiate and sustain a reaction in the presence of a low temperature catalytically active carbonaceous char having a t-¾ time less than about 15 minutes.

2. The process of claim 1 wherein the t-¾ time of said catalytically active carbonaceous char is less than about 10 minutes.

3. The process of claim 1 wherein the t-¾ time of said catalytically active carbonaceous char is less than about 5 minutes.

4. The process of claim 1 wherein said catalytically active carbonaceous char is granular, pelleted, shaped, or powdered.

5. The process of claim 1 wherein said catalytically active carbonaceous is formed, bonded, or otherwise incorporated into a unitized body for use as a filtration media.

6. The process of claim 1 wherein said catalytically active carbonaceous char is a fiber, fabric, or cloth.

* * * * *